United States Patent
Vazirani et al.

(10) Patent No.: US 12,287,273 B2
(45) Date of Patent: Apr. 29, 2025

(54) METHOD FOR OPTIMISING THE CONCENTRATION OF ELEMENTS OF INTEREST FOR VISUAL MEASUREMENT ON A BIOLOGICAL SAMPLE

(71) Applicant: ERBA DIAGNOSTICS LIMITED, Dublin (IE)

(72) Inventors: Nikhil Vazirani, Maharashtra (IN); Sylvain Andlauer, Le Cres (FR); Samantha Noel, Montpellier (FR)

(73) Assignee: ERBA DIAGNOSTICS LIMITED, Dublin (IE)

( * ) Notice: Subject to any disclaimer, the term of this patent is extended or adjusted under 35 U.S.C. 154(b) by 950 days.

(21) Appl. No.: 17/425,299

(22) PCT Filed: Jan. 23, 2020

(86) PCT No.: PCT/EP2020/051646
§ 371 (c)(1),
(2) Date: Jul. 22, 2021

(87) PCT Pub. No.: WO2020/152277
PCT Pub. Date: Jul. 30, 2020

(65) Prior Publication Data
US 2022/0136954 A1 May 5, 2022

(30) Foreign Application Priority Data
Jan. 23, 2019 (FR) ........................ 1900590

(51) Int. Cl.
*G01N 15/01* (2024.01)
*C12N 5/00* (2006.01)
(Continued)

(52) U.S. Cl.
CPC ....... *G01N 15/1404* (2013.01); *C12N 5/0087* (2013.01); *G01N 1/38* (2013.01);
(Continued)

(58) Field of Classification Search
CPC .. G01N 15/1404; G01N 1/38; G01N 15/0656; G01N 2015/016;
(Continued)

(56) References Cited

U.S. PATENT DOCUMENTS

| | | | | |
|---|---|---|---|---|
| 2005/0051466 A1* | 3/2005 | Carter | .................... | G01N 15/05 210/512.1 |
| 2015/0316477 A1* | 11/2015 | Pollak | .................... | C12Q 1/04 435/40.51 |

FOREIGN PATENT DOCUMENTS

| | | |
|---|---|---|
| WO | 2006103334 A2 | 10/2006 |
| WO | 2015001553 A1 | 1/2015 |

OTHER PUBLICATIONS

Mikrometastaselab et al: "Cytospin Pre Para Ti On", Jan. 1, 2006 (Jan. 1, 2006), XP055683190, Extra it de I Internet: URL:https://ki.projectcoordinator.net/main .php/Cytospin%20jan%202006.pdf?fileitem=27 85415 [extrait le Apr. 6, 2020] le document en entier.
(Continued)

*Primary Examiner* — Roy M Punnoose
(74) *Attorney, Agent, or Firm* — Thomas | Horstemeyer, LLP

(57) ABSTRACT

The invention relates to a method for imaging a body fluid sample for visual measurements relating to leukocytes, which comprises: —obtaining a measured concentration (WIC) of leukocytes in the sample; —diluting (330) a test solution obtained from the sample, with a dilution ratio (D) determined in accordance with the measured concentration of leukocytes in the sample, so as to obtain an optimum concentration of leukocytes; —rotating (400) the optical chamber containing the test solution by a centrifugation unit, so as to align the leukocytes of the test solution on an optical plane, wherein the optimum concentration of leukocytes for the test solution corresponds to a target surface density of
(Continued)

between 20 and 1000 leukocytes per square millimetre on the optical plane; and—imaging (500) the test solution.

14 Claims, 10 Drawing Sheets

(51) Int. Cl.
*G01N 1/38* (2006.01)
*G01N 15/06* (2006.01)
*G01N 15/1404* (2024.01)
*G01N 15/10* (2006.01)
*G01N 15/14* (2006.01)

(52) U.S. Cl.
CPC ... *G01N 15/0656* (2013.01); *G01N 2015/016* (2024.01); *G01N 2015/1006* (2013.01); *G01N 2015/1486* (2013.01)

(58) Field of Classification Search
CPC ... G01N 2015/1006; G01N 2015/1486; G01N 15/01; G01N 15/1484; G01N 15/06; G01N 15/1468; G01N 1/2813; G01N 1/30; G01N 15/12; C12N 5/0087
See application file for complete search history.

(56) References Cited

OTHER PUBLICATIONS

Martinazzi Massimo: "A Slide Centrifugation Technic for Concentrating Blood Leukocytes and Nucleated Cells from Bone Marrow Bloo", American Journal of Clinical Pathology, Dec. 1, 1971 (Dec. 1, 1971), pp. 719-722, XP009519771, ISSN: 1943-7722, DOI: 10.1093/ajcp/56.6.719; Materials and Methods, p. 719-720.
Natalie Mayhead, et al., "How to 'stick' leukocytes to a microscope slide?", ResearchGate, Jul. 7, 2012, XP055683422, Extrait de l'Internet: URL: https://www.researchgate.net/post/How_to_stick_leukocytes_to_a_microscope_slide2 (extrait le Apr. 6, 2020] post of Aiden E. Ryan and Harilaos Filippakis, on the Jul. 7, 2016.
French Search Report for co-pending related French application No. 865700, mailed Dec. 10, 2019.
PCT Search report for co-pending PC Application No. PCT/EP2020/051646, mailed Apr. 17, 2020.

* cited by examiner

FIG. 5

| WiC | Dilution method | Dilution solution volume added to S2 |
|---|---|---|
| 0.3.10^3 - 7.10^3 WBC/μL | None | None |
| 7.10^3 - 50.10^3 WBC/μL | Direct addition | 0 - 4.1 mL |
| 50.10^3 - 500.10^3 WBC/μL | Sampling of 80 μL | 0.52 - 4.92 mL |

| WBC families | Normal proportions in the blood | 61 | 62 | 63 | 64 |
|---|---|---|---|---|---|
| Neutrophils | 50% | 14.1% | 5.8% | 1.44% | 1.29% |
| Lymphocytes | 30% | 18.3% | 7.5% | 1.86% | 1.67% |
| Monocytes | 14% | 26.7% | 10.9% | 2.73% | 2.44% |
| Eosinophils | 5% | 44.7% | 18.3% | 4.56% | 4.08% |
| Basophils | 1% | 100.0% | 40.8% | 10.21% | 9.13% |

# METHOD FOR OPTIMISING THE CONCENTRATION OF ELEMENTS OF INTEREST FOR VISUAL MEASUREMENT ON A BIOLOGICAL SAMPLE

CROSS REFERENCE TO RELATED APPLICATIONS

This application is the 35 U.S.C. § 371 national stage application of PCT Application No. PCT/EP2020/051646, filed Jan. 23, 2020, which application claims the benefit of French Application No. FR 1900590, filed Jan. 23, 2019, both of which are hereby incorporated by reference herein in their entireties, including any figures, tables, nucleic acid sequence, amino acid sequences, or drawings.

FIELD OF THE INVENTION

The invention concerns the analysis of a body fluid to count and identify elements of interest, especially in haematology for counting cells and differentiating leukocytes and erythrocytes. The invention relates to a method for improving the imaging of a body fluid sample, as well as an associated method and computer program product.

STATE OF THE ART

Many human or animal diseases correspond to an abnormal quantity of leukocytes or erythrocytes in the blood, or to an abnormal distribution of leukocytes among the five known subgroups: lymphocytes, monocytes, basophils, eosinophils and neutrophils. For example, a high concentration of lymphocytes in a blood sample can be correlated to an immune response.

The various subgroups of blood cells are distinguished, in particular, by their average size, their membrane complexity and by the number of cellular nuclei (anuclear, mononuclear and polynuclear cells). Very reliable differentiation results for the elements of interest can be obtained by human visual analysis. However, we are seeking to limit human intervention and the associated time and expense as much as possible. Moreover, the statistical power of a differentiation performed with the naked eye is not satisfactory for medical applications.

Precise count and differentiation results can be obtained by automated methods. Automation is indispensable for high-speed analysis applications.

The majority of known automated methods rely on an optical measurement performed on a blood sample. It is common to perform measurements of the resistivity or optical diffraction of the sample. Patent document FR 2,883,972 describes (in relation to FIGS. 4 and 5) an optical device making it possible to detect the light diffracted by a biological sample according to several angles and several wavelengths. Leukocyte differentiation is then performed on the basis of the diffraction measurements. Patent document U.S. Pat. No. 5,812,419 describes (for example in relation to FIG. 31) a flow cytometry cell designed to perform optical measurements on a biological sample.

Flow cytometry measurement has the advantage of a high speed. However, a major defect is the difficulty of verifying the analysis results. Optical signals are computer-processed and a result of the distribution of elements of interest among the subgroups is provided to the user, with no intuitive way for the user to verify the results.

Thus, these state of the art systems operate as a "black box". Several artifacts can decrease the reliability of the differentiation. The analysis results are often presented in the form of a cloud of points in two dimensions, in which segmentation into subgroups or "clusters" is performed; if these clusters are partially superimposed, the estimate of the distribution among the subgroups may be distorted.

Aware of the limits of these systems, many actors in the field only use them as a first step to filter problematic samples. Subsequently, they often conduct an additional visual analysis or "slide review" by an operator on a non-negligible part of the blood samples to be analyzed which can reach up to 30% of samples.

This situation is unsatisfactory in terms of speed, especially if the proportion of pathological samples is high, which is likely to occur when the analysis is done in a hospital or specialized laboratory.

To automate the "slide review" and to limit the need for additional analysis by operators, counting and differentiating the elements of interest by visual measurements has been proposed, from microscopic images of blood samples in which the elements of interest are highlighted.

Patent document WO 2010/126903 describes a method comprising applying a blood sample onto a slide (after leukocyte staining) and spreading the sample along the slide, to create a reading zone. For example, the reading zone comprises around 600 cells in the case where the elements of interest are leukocytes. The reading zone on the slide is photographed and subjected to an automatic image analysis. The photographs are enlarged at the leukocyte level to detect a size and shape of leukocytes in order to differentiate the leukocytes.

Visual elements permit advanced morphological characterization of the elements of interest. Performing leukocyte differentiation (lymphocytes, monocytes, basophils, eosinophils and neutrophils) in this way is known. Visual measurements are also relevant for other types of elements of interest, such as immature erythrocytes like erythroblasts or reticulocytes, or even to detect the presence of parasites (malaria) characterized by the presence of DNA/RNA in the erythrocytes. The morphological characterization of erythrocytes is also relevant in the case of sickle cell anaemia or anaemia.

The visual measurement method of document WO 2010/126903 has several disadvantages, however. It is necessary to obtain and record numerous enlarged images of the slide, which takes time for the movement of the slide in order to observe each cell of interest. The analysis time for a sample is therefore considerable, especially if it is necessary to count numerous cells of interest per sample.

Moreover, the statistical value of the distribution obtained decreases if the leukocyte concentration is too low, since there are not enough leukocytes available in the photographs to determine a reliable distribution, which reduces the precision of the result. Conversely, if the leukocyte concentration is too high, the leukocytes can be superimposed on the slide and their size and shape is not correctly detected and reliability is thus lost.

The current means to automate "slide review" therefore are not completely satisfactory.

GENERAL DESCRIPTION OF THE INVENTION

There is therefore a need for automatic analysis of a body fluid sample giving very reliable count and differentiation results for elements of interest (especially leukocytes), in order to maximally reduce the need for human visual analysis.

Reliable results are obtained while avoiding "black box" operation: the results of the visual measurement of leukocytes should be verifiable by a human observer to allow detection of artifacts on the processing line that would be likely to distort the measurement.

There is an additional need for a method of imaging elements of interest (including leukocytes) which is adjusted to the initial leukocyte concentration of the sample, which is variable and initially unknown. However, the measurements should remain reliable.

In particular, precise results are desired, including from samples initially comprising few or many leukocytes by volume.

There is another additional need for a method that limits the amount of slide reviews while performing visual measurements at a high speed, not requiring extracting too many enlarged images.

To this end, the invention concerns, according to a first aspect, a method for imaging a body fluid sample for visual measurement relating to elements of interest of the sample, comprising the following steps:
- an acquisition of the concentration in elements of interest of a solution derived from the sample, resulting in obtaining a measured concentration of the elements of interest in the sample;
- a dilution of a test solution derived from the sample, according to a dilution ratio determined as a function of the measured concentration of elements of interest in the sample, so as to bring the concentration of elements of interest in the test solution to an optimal concentration;
- imaging, by an imaging device, of the test solution transferred into an optical chamber.

The method of the invention thus comprises an automatic dilution that is specific to the sample (adjustment dilution), based on the concentration of elements of interest in the initial sample, to adjust the concentration of the test solution derived from the sample. Imaging is then done on the test solution that was subjected to the adjustment dilution.

This adjustment ensures that the test solution in the optical chamber is appropriate to perform visual measurements and guarantees the statistical precision and reliability of the measurements.

One advantage of the method according to the invention is therefore to limit the impact of variations of the initial concentration of elements of interest of the sample on the quality of visual measurements. The method is particularly advantageous in the case where the elements of interest are leukocytes, since their concentration can vary by up to a factor of 200 depending on the disease. The range of leukocyte concentrations observable in the blood of different human individuals is very extensive, so that it is particularly relevant to do an adjustment dilution in the case where the elements of interest to be observed are leukocytes.

Images of individual elements of interest are then quickly extractable from the test solution imaging. The method of the invention therefore makes it possible to optimize the analysis speed by limiting the number of image captures necessary, since the speed is obtained as a number of samples analyzed per unit of time.

Thus, an optimal density of elements of interest can be obtained in the images, while maintaining a high speed, regardless of the initial concentration of elements of interest. It is thus possible to reduce the proportion of samples to be analyzed that must be subjected to "slide review" by a human operator to 2%.

The method of the invention, combined with the adjustment dilution, is also advantageous to perform a qualitative analysis on the biological sample. Indeed, the imaging done allows qualitative visual measurements on the elements of interest or on other elements of the image, for example a characterization of the quality and/or health status of the elements of interest and/or other elements.

Visual measurements combined with the adjustment dilution therefore make it possible to provide relevant clinical data, optionally quantitative and qualitative, while ensuring an optimum analysis speed and good statistical precision of the measurements.

Additional and non-limiting features of the imaging method of the invention are as follows, taken alone or in one of the technically possible combinations:
- the method comprises an additional step, prior to imaging, of concentrating the elements of interest of the test solution on the same optical plane perpendicular to a direction of thickness of the optical chamber.
- the method comprises a step of rotating the optical chamber by a centrifugation unit after the transfer of the test solution into the optical chamber, so as to align the elements of interest (preferably leukocytes) of the test solution on an optical plane comprised in the optical chamber, the optical plane being perpendicular to a direction of thickness of the optical chamber.

Centrifugation performed by the centrifugation unit makes it possible to automatically and quickly align the elements of interest, preferably leukocytes, on the optical plane of the optical chamber.

By means of the adjustment dilution of the test solution (performed according to the concentration measured of elements of interest in the initial body fluid sample) combined with the centrifugation step, it is possible to bring the surface density of the elements of interest on the optical plane to a target surface density, regardless of the concentration of elements of interest measured in the initial sample.

Obtaining such a target surface density ensures that the coverage rate of the elements of interest in the images derived from imaging is not too high, while ensuring that a sufficient number of elements of interest are visible in said images. Thus the relevance of the subsequent visual measurements is improved;
- the optimal concentration of leukocytes for the test solution corresponds to a target surface density on the optical plane comprised between 30 elements of interest per square millimetre and 1000 elements of interest per square millimetre, at the end of the alignment of the elements of interest on the optical plane.
- the optical chamber is rotated for a duration comprised between 5 seconds and 5 minutes, preferably comprised between 10 seconds and 1 minute.
- the acquisition comprises a non-visual measurement on an intermediate solution derived from the sample, preferably an impedance measurement by a micro-orifice.
- the acquisition comprises a measurement of the absorbance at a predetermined wavelength on an intermediate solution derived from the sample, said wavelength being preferably 540 nanometres.
- the dilution ratio D is calculated from the WIC measured concentration of elements of interest in the sample using the following formula:

$$D=WIC*h/WPD,$$

where h is the height of the optical chamber and WPD is the target surface density on optical plane PO.

the dilution ratio D is calculated from the WIC measurement of the concentration of elements of interest in the sample using the following formula:

$$D = WIC * V/WPC,$$

where V is the volume of the optical chamber and where WPC is an optimal number of leukocytes in an image. —the process comprises a step of comparing the concentration measured in elements of interest of the sample to a threshold, the dilution of the test solution derived from the sample being done according to the result of said comparison.

the dilution ratio D is comprised between 10 and 1000.

the elements of interest are leukocytes.

the elements of interest are under-represented in the sample (in the case of leukocytes in human blood), and the method comprises an additional step of preparing the test solution comprising cell separation and/or selective chemical and/or physical lysis to sort the cells and retain the elements of interest.

The method of the invention, combined with lysis of sample erythrocytes, is particularly advantageous in the context of morphological analysis of leukocytes (the elements of interest then being leukocytes), since leukocytes are 1000 less numerous than erythrocytes or thrombocytes in human blood.

Thus, by lysis of erythrocytes before imaging the sample, the subsequent visual measurements on the leukocytes are optimized in terms of quality and density of the elements of interest. Notably, if a surface density comprised between 20 leukocytes per square millimetre and 1000 leukocytes per square millimetre is obtained on the optical plane of the optical chamber prior to imaging, it is advantageous to implement the cell sorting step to eliminate erythrocytes that would greatly reduce the quality of the visual measurements.

the image obtained at the end of imaging has a total number of leukocytes comprised between 5 and 200, preferably comprised between 140 and 160.

the imaging step comprises a plurality of image acquisitions at distinct positions of the imaging device relative to the optical chamber, the imaging device moving along the same direction between two consecutive positions.

the method comprises a visual measurement performed on the test solution image, the visual measurement preferably comprising a differential count of the elements of interest, a result of said count comprising a distribution of the elements of interest in the sample among a plurality of subgroups.

the procedure contains an additional step of preparing the test solution comprising permeabilization of the membranes of the elements of interest and/or a distinctive staining of the elements of interest.

the elements of interest are erythrocytes or thrombocytes.

According to a second aspect, the invention concerns an imaging system relating to the elements of interest of a body fluid sample, comprising:

a device for measuring the concentration in elements of interest of a body fluid sample, a dilution device designed to perform a dilution of a solution derived from a body fluid according to a determined dilution ratio, an optical chamber designed to receive a test solution derived from a body fluid sample, an imaging device, a processor configured to control the imaging device and to receive, from the measurement device, a measurement of the concentration of elements of interest of the sample, the processor being further configured to calculate a dilution ratio depending on said measurement.

Additional and non-limiting features of the system of the invention are as follows, taken alone or in combination:

the system also comprises a centrifugation unit configured to rotate the optical chamber containing the test solution.

the device for measuring the concentration of elements of interest comprises a micro-orifice cell, designed to determine a count of elements of interest by impedance.

the imaging device comprises movement means designed to move an objective of the imaging device along a reading axis of the optical chamber.

the optical chamber comprises a leukocyte support wall delimiting an optical plane, the leukocyte support wall having a thickness comprised between 0.05 millimetres and 0.5 millimetres, the centrifugation unit being configured so as to bring the leukocytes of the test solution onto said optical plane.

According to a third aspect, the invention concerns a non-transitory computer-readable storage medium storing code instructions which, when the code instructions are executed by a processing unit, lead the processing unit to implement an imaging method as defined above.

GENERAL DESCRIPTION OF THE FIGURES

Other features, objectives and advantages of the invention will appear from the following description, which is purely illustrative and non-limiting and should be read with regard to the attached drawings, among which:

FIG. 1 schematically shows a system for imaging samples of body fluids such as blood samples, according to one embodiment of the invention;

FIG. 2 illustrates the steps of lysis and centrifugation of a blood sample. The left column relates to a sample of low leukocyte concentration. The right column relates to a sample of high leukocyte concentration.

FIG. 5 is a comparative table of the dilution protocols adjusted for various concentrations in cells of interest of the blood sample;

DETAILED DESCRIPTION OF THE INVENTION

The description below mainly concerns the preparation of a haematology solution from a blood sample, to perform measurements of the differentiation and morphology of elements of interest, here leukocytes. However, the invention also applies to any fluid sample, especially body fluid, comprising elements of interest on which visual measurements are to be performed such as cells, casts, parasites, etc. These elements of interest are typically in suspension in body fluids such as blood, urine, lymph, amniotic fluid, etc. The elements of interest are pathological (blasts, lymphomas, etc.) or non-pathological.

In the following, "visual measurements" are measurements performed from images acquired in a solution derived from the sample, in which the elements of interest (optionally labeled) are visible. The visual measurements are performed from one or more images of the solution, preferably automatically, by image analysis.

In the description below and in the attached figures, similar elements are designated by the same alphanumeric references.

System for Preparation of a Haematological Solution and Imaging

Figure 1:
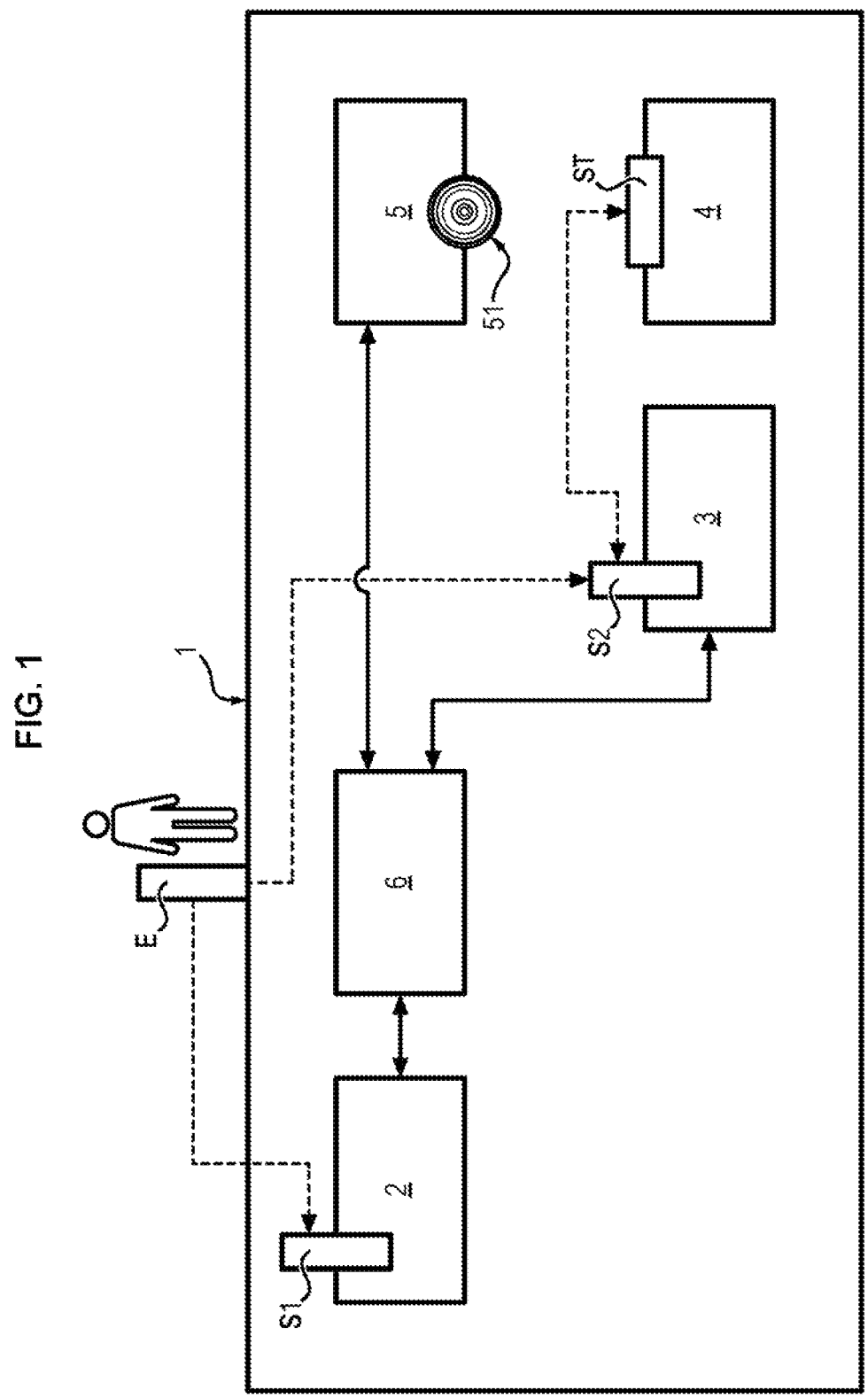

FIG. 1 shows a system 1 for preparing a test solution ST and acquiring images of test solution ST, from a blood sample E drawn from an individual, for example in haematology. System 1 of FIG. 1 can be used in a medical analysis laboratory, to obtain results to aid diagnosis of a possible disease of the individual.

System 1 comprises a measurement device 2 performing haematology measurements. Measurement device 2 is configured to acquire preliminary haematological measurements on an intermediate solution S1 derived from sample E. The preliminary measurements comprise a leukocyte concentration. Solution S1 is derived, for example, from a dilution of sample E.

Preferably, measurement device 2 comprises a cell bearing a 100-µm diameter orifice, a so-called "micro-orifice", the micro-orifice cell being configured so as to perform a leukocyte count by impedance. Impedance counting is a non-visual approach to measurement of the leukocyte concentration of intermediate solution S1. One advantage of impedance measurement is the high processing speed of the analog signal performed by a dedicated microprocessor.

From the leukocyte concentration of solution S1 and knowing the dilution ratio between sample E and solution S1, a "white blood cell impedance count" (WIC) of the leukocyte concentration in sample E can be obtained with measurement device 2.

The WIC measurement gives a result considered to be reliable for the count of elements of interest (leukocytes here). However, the results of the differentiation provided by an impedance count are considered unsatisfactory for the reasons discussed above in the introduction.

The system of FIG. 1 also comprises a dilution device 3, an optical chamber 4 and a photographic device 5.

Dilution device 3 is designed to perform a dilution of a fluid sample, by addition of dilution solution to a given volume of intermediate solution S2 derived from sample E. Said intermediate solution S2 is derived from the chemical and/or physical preparation of sample E—the chemical and/or physical preparation being performed, according to one possible variant, at the same time as the dilution enabling solution S1 to be obtained. Here, dilution device 3 enables the dilution of sample E to obtain an intermediate solution S2, then an adjustment dilution of sample S2 to obtain a test solution ST.

Alternatively, the first dilution to obtain intermediate solution S2 from sample E is performed by a device different from the one dedicated to the adjustment dilution to obtain a test solution ST from intermediate solution S2. Advantageously, the dilution ratio applied to solution S2 is chosen as a function of an optimal concentration of leukocytes desired for test solution ST.

System 1 also comprises a processing unit 6. Note that in the example of FIG. 1, devices 2, 3, 4 and 5 of processing unit 6 are comprised in a same enclosure of system 1. System 1 is an automated diagnostic device, for example.

Figure 2:
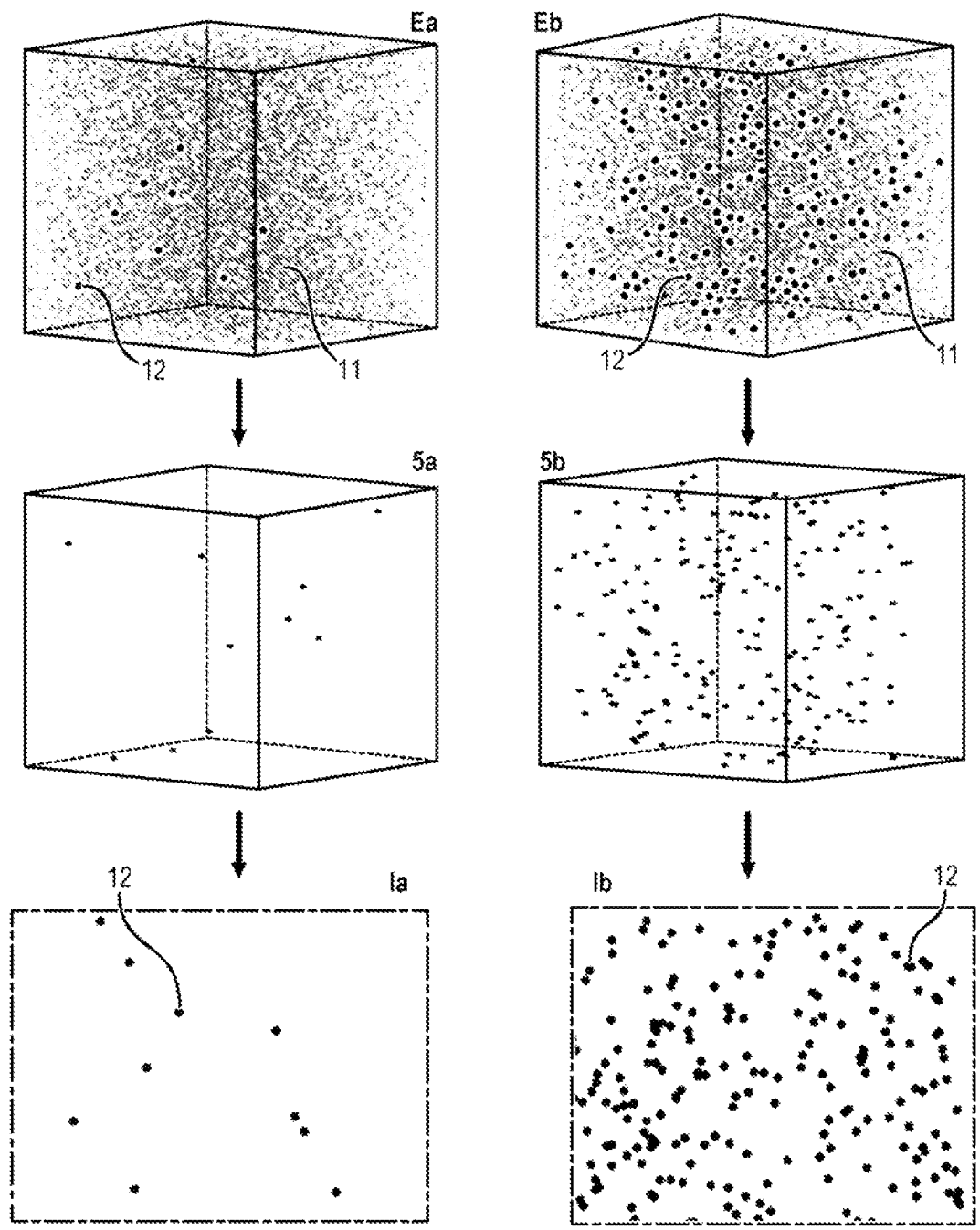

FIG. 2 compares the results of images obtained for a blood sample of low leukocyte 12 concentration (left) and for a sample of high leukocyte 12 concentration (right). No adjustment dilution was performed. In other words, FIG. 2 concerns samples for which the dilution ratio has not been adjusted according to the initial leukocyte concentration. Samples Ea and Eb also comprise erythrocytes 11. On average, the erythrocyte concentration is 1000 times greater than the leukocyte concentration.

Solutions 5a and 5b are represented, derived from a lysis of erythrocytes, respectively from samples Ea and Eb, as well as images Ia and Ib respectively acquired from solutions 5a and 5b. In image Ia, insufficient leukocytes are available to perform a reliable leukocyte differential count. Conversely, the leukocyte concentration is too high in image Ib and the leukocytes are superimposed in places, distorting the count and morphological measurements. By adjusting the leukocyte concentration (preferably jointly with erythrocyte lysis), the visual measurements subsequently performed on the images can be improved and facilitated.

Dilution device 3 makes it possible to add the dilution solution (in the example below, diluent comprising, for example, a lysis agent and/or a staining agent) to a liquid sample.

It is relevant to add the lysis agent at the time of dilution of a biological sample if all the cells that were to be eliminated by a preceding lysis have not been correctly eliminated. Indeed, the addition of diluent can cause the reappearance of the residues of incorrectly cells.

Here, dilution device 3 comprises a container having an opening at a first end to receive a volume of blood and a volume of diluent, and having a tube at a second end to inject bubbles into the container and stir the blood/diluent mixture. Dilution device 3 here comprises an additional tube to extract the blood/diluent mixture after dilution. In the present example, a maximum volume of fluid contained in the container is 5 millilitres.

Alternatively, devices 3 and 4 can be used for the observation of erythrocytes (and not only leukocytes), in which case intermediate solution S2 would be prepared from sample E differently.

Figure 3A:
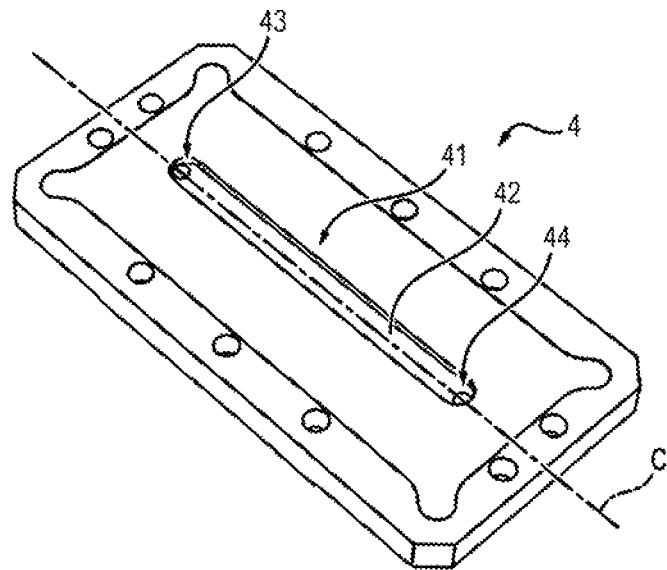
FIG. 3a is a top perspective view of an optical chamber of the system of FIG. 1.

Optical chamber 4 is shown in FIG. 3a (without its cover) in perspective top view. Optical chamber 4 is show in FIG. 3b in longitudinal section along plane C shown in FIG. 3a.

Optical chamber 4 comprises two circular openings 43 and 44 between which a reading channel 42 extends. Openings 43 and 44 make it possible to transfer fluid from the outside. Reading channel 42 comprises two vertical portions directly below openings 43 and 44, these two portions being joined by a horizontal portion of channel 42 that extends along reading axis A of the optical chamber. The horizontal portion preferably has a thickness e comprised between 0.05 millimetres and 10 millimetres, for example between 0.1 millimetres and 10 millimetres, for example 1 millimetre. Opening 43 thus constitutes an inlet port and opening 44 constitutes an outlet port for a volume of solution contained in reading channel 42.

Optical chamber 4 is closed on top by an upper face 41 and on the bottom by a thin optical wall. The upper and lower faces are transparent to visible light along reading channel 42. In order to close the optical chamber, a cover (not shown) is optionally positioned against the optical wall.

Figure 3B:
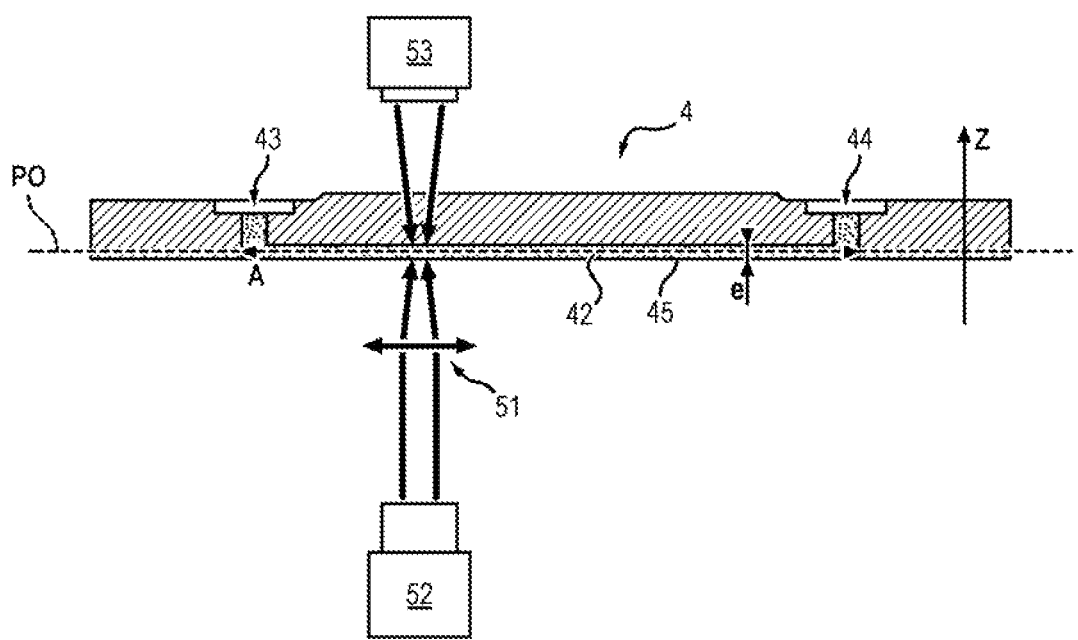
FIG. 3b is a schematic side view of the same optical chamber associated with an imaging device.

A total height of optical chamber 4 along direction Z visible in FIG. 3b is preferably comprised between 500 and 1500 micrometres, said direction Z being perpendicular to optical plane PO. In the present example, the total height of optical chamber 4 along direction Z is equal to 1000 micrometres.

Photographic device 5 comprises a chamber 52 equipped with a photographic sensor and comprises an objective 51. This device is used with a light source 53. Photographic device 5 comprises a memory to record images $I_n$ acquired, the images being transmitted to the processing unit 6.

In the present example, objective 51 is an objective with strong achromatic correction and 20× magnification. Generally, an objective 51 with a magnification comprised between 10× and 50× is considered to be suitable to obtain a satisfactory number of elements of interest per image, as will be seen below.

Furthermore, objective 51 preferably has a numerical aperture comprised between 0.4 and 0.6. In the present example, said numerical aperture is 0.5.

Once test solution ST is transferred into the reading channel and ready to be photographed, photographic device 5 is disposed in the vicinity of optical chamber 4 so as to image the internal volume of reading channel 42.

Photographic device 5 is here positioned below reading channel 42, objective 51 being directed toward the reading channel. Light source 53 is placed behind the reading channel, on the other side of the optical chamber. Preferably, light source 53 emits a combination of monochromatic light or even a white light.

FIG. 3b shows an optical plan PO passing through wall 45, wall 45 delimiting the bottom of reading channel 42.

Very advantageously, to improve the visibility of elements of interest in the images acquired by photographic device 5, test solution ST is prepared before imaging, so as to align the elements of interest on optical plane PO perpendicular to direction of thickness Z of channel 42.

Wall 45 delimiting the bottom of channel 42 therefore serves as support wall for the cells of interest (i.e., leukocytes here) after preparation of test solution ST.

The preparation and imaging system for the test solution thus comprises a device for moving the elements of interest of the test solution at optical plane PO. Here, optical chamber 4 can be driven by a centrifugation unit (not shown) to accelerate the natural sedimentation along the optical measurement axis, to bring the cells of interest (such as leukocytes) of test solution ST against wall 45.

The centrifugation unit is preferably configured to rotate optical chamber 4 around an axis of rotation parallel to optical plane PO. Alternatively or in combination, as the device intended to align the elements of interest on optical plane PO, a filtration device or microfluidic device can be used.

Preferably, wall 45 has a thickness along direction Z comprised between 0.05 millimetres and 0.5 millimetres. Still more preferentially, said thickness is comprised between 0.1 millimetres and 0.3 millimetres, and is here equal to 0.2 millimetres.

With a thickness value close to 0.2 millimetres, the depth of field (DOF) of objective 51 of photographic device 5 can be chosen between 2.7 and 3.0 micrometres.

Preferably, photographic device 5 also comprises movement means (not shown) designed to move objective 51 and chamber 52 along a direction located vertically to reading axis A. It can be a rail. The field of view of objective 51 is moved along axis A. One advantage of this configuration is to make it possible to acquire a plurality of images that cover all of reading channel 42.

Photographic device 5 also preferably comprises means for moving objective 51 along direction of thickness Z of channel 42 to improve focussing.

To return to FIG. 1, processing unit 6 is configured to control photographic device 5, for example a server. Processing unit 6 sends imaging, and optionally moving, instructions to photographic device 5. The processing unit also comprises a memory to store images $I_n$ provided by device 5.

Processing unit 6 is also configured to receive a leukocyte concentration measurement of sample E from measurement device 2, or, alternatively, to determine this measurement from a preliminary measurement provided by measurement device 2. Processing unit 6 is also configured to calculate an optimal dilution ratio D from the leukocyte concentration measurement of the sample, according to the protocols described below.

Processing unit 6 is configured with computer program code instructions to perform the functions noted above.

Preferably, processing unit 6 also comprises computer means configured to perform visual measurements from images I acquired on test solution ST. In the present example, the calculation means are configured to determine, from images I, several parameters of interest:
- a leukocyte count, i.e., a total leukocyte concentration;
- a differential count (or differentiation) of leukocytes, i.e., a distribution of leukocytes into five subgroups: lymphocytes, monocytes, basophils, eosinophils and neutrophils;
- the morphological characteristics of leukocytes, for example from membrane structure information for leukocytes belonging to the various subgroups, or on the structure of the nucleus or nuclei;
- a detection of interferences related to the method, such as detection of erythrocytes that would indicate a potential resistance to the lysis used in the method.

Alternatively, processing unit 6 is connected, by hardwired or wireless connection, to a computer unit configured to perform visual measurements on leukocytes.

The haematological measurement provided by device 2 and the visual measurement obtained from images $I_n$ respectively correspond to two separate measurement approaches.

The system of FIG. 1 can optionally be supplemented by other measurement methods. Additional measurement approaches can correspond to other types of elements of interest, especially erythrocytes; for example device 2 can be a cell comprising an orifice of 78 μm in diameter, configured to perform an impedance count of erythrocytes and thrombocytes.

Method for Preparation of a Test Solution and Imaging

Figure 4:
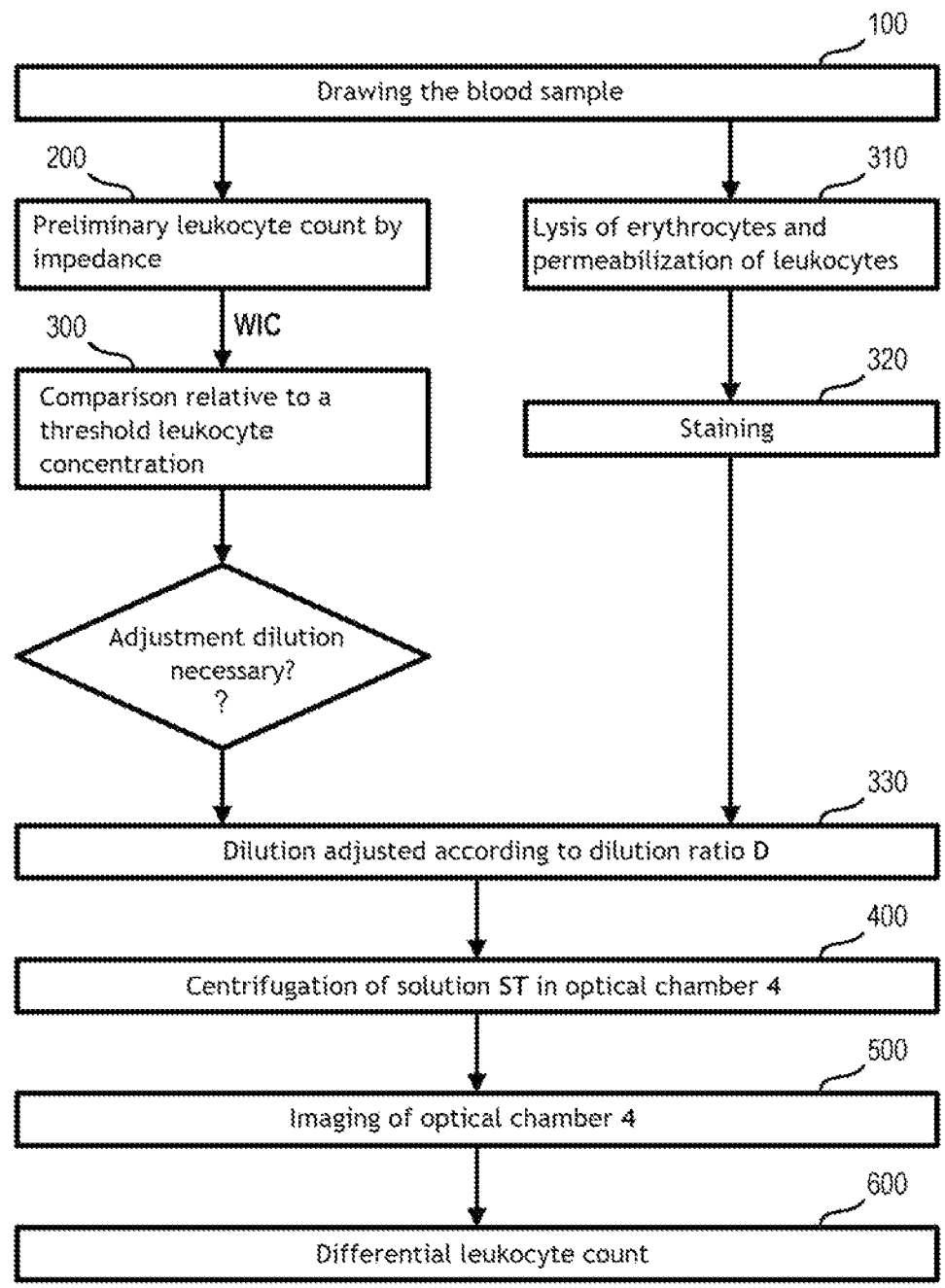
FIG. 4 illustrates the steps of a method for imaging and visual measurement on a blood sample, according to one embodiment of the invention.

FIG. 4 shows the steps of an imaging method from a blood sample, in view of performing visual measurements on leukocytes, according to one embodiment of the invention.

The sample preparation and imaging system of FIG. 1 is designed to implement the method of FIG. 4.

Preferably, all the steps of this method—except optionally preliminary step 100 of drawing the blood sample—are performed automatically by system 1. As indicated above, system 1 is preferably an automated diagnostic device.

Thus blood sample E provided to system 1 can be a pure blood sample. Once blood sample E is provided to system 1, human intervention is preferably not necessary until the images are obtained. Measurement device 2, dilution device 3, optical chamber 4 and imaging device 5 are preferably controlled so as to implement the method of FIG. 4 in a coordinated manner.

The preparation of test solution ST described below, notably comprising an adjustment dilution at step 330, does not require human intervention. Dilution device 3 is configured to automatically optimize the dilution performed, as a function of the leukocyte concentration measured in sample E, as will be seen below.

At a preliminary step 100, a sample E is drawn from an individual. It is understood that the following steps can be performed at a time and place different from the one of drawing the sample.

Conforming to the invention, an acquisition of the concentration of elements of interest of sample E is performed in a step 200.

Here, we are talking about acquisition giving a preliminary measurement of the concentration of elements of interest (leukocytes here), because this measurement is done prior to the visual measurements for leukocyte differentiation.

For example, step 200 is here an impedance measurement, to obtain a leukocyte count. The impedance measurement is done here on an intermediate solution S1, obtained by dilution of sample E (to obtain approximately 1600 microlitres of diluted solution) then by addition of a volume of erythrocyte lysis solution (for example 200 microlitres of the lysis solution).

The lysis solution advantageously contains an additional cyanide-free compound for the quantification of haemoglobin. This compound forms complexes with the haemoglobin of the solution. An absorbance measurement, for example at 540 nm, permits evaluating the quantity of complexes thus formed.

Step 200 provides a preliminary "white blood cell impedance count" (WIC) measurement of the leukocyte concentration in sample E, in number of cells per microlitre.

As indicated above in relation to FIG. 2, the performance of visual measurements varies according to the leukocyte concentration of sample E.

For a non-pathological sample, whose leukocyte activity can be considered normal, it is estimated that the WIC measured concentration is between 3500 and 11,000 leukocytes per microlitre, for a human being.

It has been observed that, in the general case, this WIC measurement can vary between 300 and 500,000 leukocytes per microlitre, when pathological samples are also included.

As a result, it should be determined whether it is necessary to do an adjustment dilution of the test solution in order to optimize the leukocyte concentration of the test solution.

Preferentially, a certain target surface density of elements of interest (leukocytes here) is to be obtained on an optical plane photographed during imaging, regardless of the initial concentration of elements of interest in sample E. As will be seen below, a target surface density of leukocytes on optical plane PO, called WPD, is preferably comprised between 20 and 1000 leukocytes per square millimetre, and is here equal to 570 leukocytes per square millimetre.

Here, at step 300, the WIC measurement is compared to a threshold for the leukocyte concentration in sample E. This threshold advantageously corresponds to an optimal quantity of elements of interest acquired by device 5; here the desired quantity in an image is determined by the size of the sensor chosen.

In the system of FIG. 1, the field of view of objective 51 is 0.5 millimetre wide and 0.7 millimetre long.

The thickness of reading channel 42 of optical chamber 4 is chosen according to the desired number of leukocytes per image (at the end of imaging step 500 which will be described below). The leukocyte concentration of test solution ST on which the imaging is done is expressed in number of leukocytes per microlitre.

Due to a default dilution of 1/12 between sample E and test solution ST, a maximum threshold of 5000 cells per microlitre is obtained for sample E.

In the present example, if the leukocyte concentration of sample E is greater than the maximum threshold, it is determined that an adjustment dilution is preferable. "Adjustment dilution" means that dilution ratio D, and therefore the volume of the dilution solution (diluent here) to be added, is determined depending on the WIC measured leukocyte concentration in sample E to adjust the concentration of test solution (ST).

Thus, the WIC measurement can be compared to a maximum threshold beyond which the risk of obtaining images saturated in leukocytes is considered to be high. In this case, the areas containing overlap of the elements of interest in the images are excluded from imaging.

The preparation of test solution ST intended for imaging therefore depends on the result of the comparison done in step 300.

If the preliminary WIC measurement is above the maximum threshold of cells per microlitre, test solution ST is obtained by performing an adjustment dilution, from an intermediate solution S2 derived from sample E.

Thus, the impedance measurement provided by device 2—which is a non-visual measurement—is skillfully exploited to prepare test solution ST before performing the visual measurements. To prepare test solution ST from sample E, an intermediate solution S2 is preferably prepared in a step 310. To obtain intermediate solution S2, a volume of lysis solution is first added to a volume of blood extracted from sample E.

For example, the lysis solution comprises an aqueous neutral buffer solution, at a hypotonic concentration. The erythrocytes are then lysed.

An agent for solubilization of the erythrocyte membranes and/or a agent for permeabilization of the leukocyte membranes can be added.

One advantage of selective lysis of erythrocytes is to allow the majority of blood cells visible in the images to be leukocytes.

Preferably, the amount of erythrocytes in the images at the end of imaging (of the total number of cells visible) is less than 10%. Preferentially, the amount of erythrocytes is approximately zero, and only a few very isolated erythrocytes remain visible in the images derived from the imaging.

In the case where erythrocytes are to be imaged as the cells of interest instead of leukocytes, lysis step 310 is omitted.

To highlight the elements of interest, a step 320 of staining the solution obtained after erythrocyte lysis is performed. In the present example, one or more anionic stains and one or more cationic stains are combined. Either of these stains can also be used alone. These stains are used sequentially to bind to the elements of interest, preferentially in the order of anionic then cationic.

Preferentially, steps 310 and 320 of preparing test solution ST from initial sample E do not comprise the use of fluorescence markers. Indeed, via the adjustment dilution of test solution ST described below, the visibility of leukocytes in the images obtained from the imaging is satisfactory, without it being necessary to use such markers.

At the end of steps 310 and 320, intermediate solution S2 is obtained. If it was determined in step 300 that it is necessary to adjust the dilution to obtain test solution ST, an adjustment dilution step 330 is performed for intermediate solution S2, using dilution device 3.

Advantageously, dilution ratio D used to go from intermediate solution S2 to test solution ST is calculated from the WIC measurement of the leukocyte concentration obtained at the end of step 200, using the formula:

$$D=WIC*h/WPD,$$

where h is the height of optical chamber 4, and where WPD (for "white blood cell picture density") is a target density of leukocytes per unit of surface on optical plane PO where images $I_n$ are acquired.

Height h, corresponding to the thickness of optical chamber 4, is, for example, 1 millimetre.

For example, an equation for dilution ratio D as a function of the WIC measurement of the leukocyte concentration (in leukocytes per microlitre) is as follows: $D=0.0018*WIC$.

Figure 6:
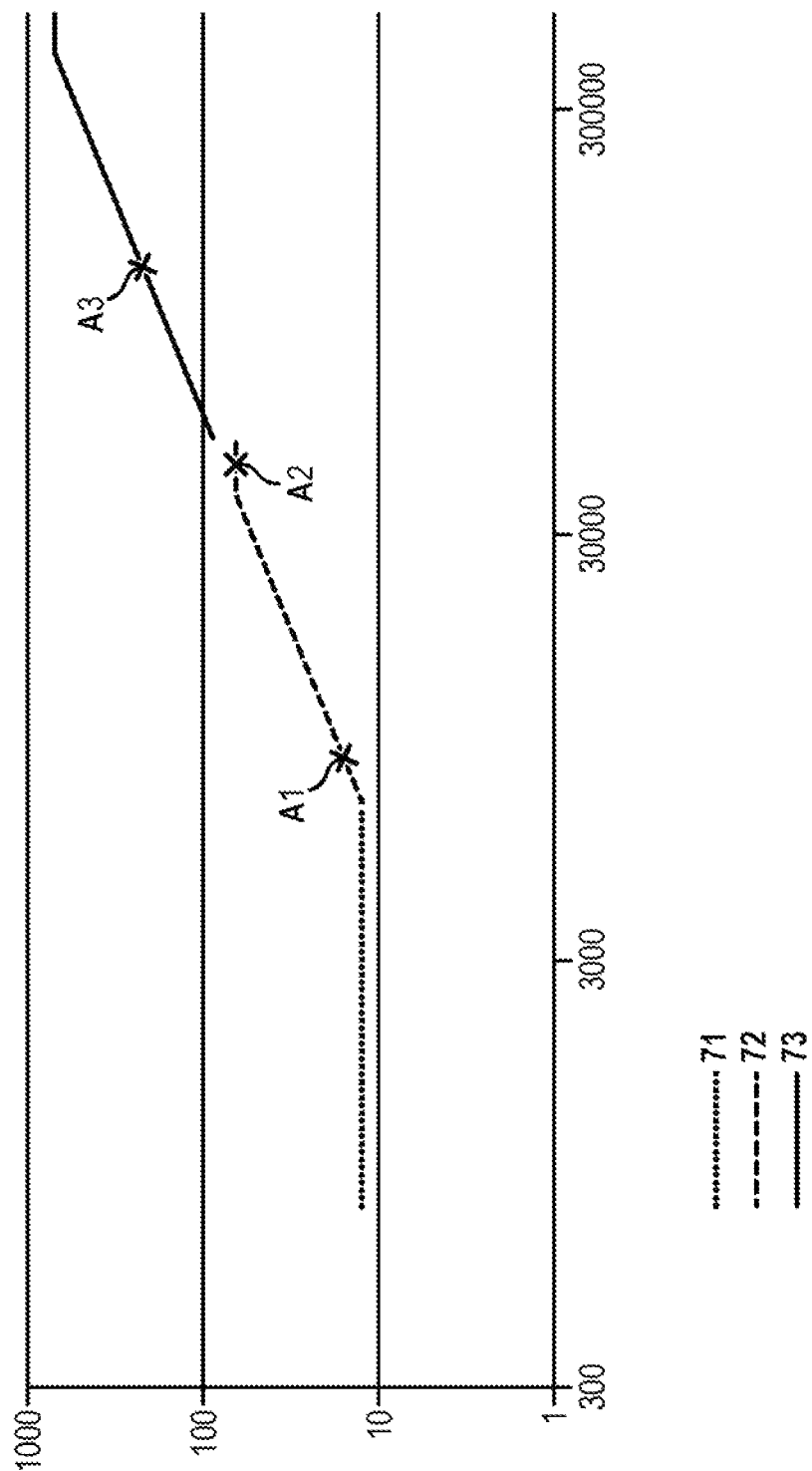
FIG. 6 is a graph that shows on the y-axis the dilution ratio applied to perform the desired concentration adjustment and obtain the test solution, and on the x-axis the leukocyte concentration leukocytes measured in an initial blood sample, according to one example of embodiment.

In the example of FIG. 6 described below, the dilution ratio is determined according to the equation $D=0.0018*WIC$ when the WIC measured concentration of leukocytes in initial sample E is greater than or equal to 7000 leukocytes per microlitre.

Adjustment dilution 330 is performed by adding a volume of diluent determined as a function of dilution ratio D.

The table of FIG. 5 gives, for example, as a function of the preliminary WIC measurement of the leukocyte concentration in sample E (left column) in number of leukocytes per microlitre:
- the preferential dilution method used in step 330: direct addition of the dilution solution, or prior sampling of a small volume of intermediate solution S2 and addition of dilution solution into this small volume;
- the volume range of the dilution to be added. This volume directly depends on dilution ratio D determined according to the formula above.

For example, for a WIC measurement of the leukocyte concentration in sample E equal to 8000 cells per microlitre, a volume of diluent equal to 180 microlitres is added to go from intermediate solution S2 to test solution ST.

Preferably, if the WIC measurement of the leukocyte concentration in sample E is greater than 38,000 cells per microlitre, a dilution is performed according to a variable dilution ratio from a volume extracted from solution S2. Indeed, for such a concentration, an addition of diluent directly into solution S2 is not sufficient to obtain optimal images, and a sampling of S2 must be done. As described in FIG. 5, for a leukocyte concentration below the maximum threshold of cells per microlitre (7000 leukocytes per microlitre in sample E), preferably the lysed and stained intermediate solution S2 is directly used as test solution ST without additional dilution.

FIG. 6 illustrates an example in which dilution ratio D is calculated in step 330 as a function of the WIC measured leukocyte concentration of initial sample E (in leukocytes per microlitre), according to the equation $D=0.0018*WIC$.

A first section 71 of the curve representative of dilution ratio D corresponds to a first operating procedure, in which test solution ST is obtained without additional dilution of intermediate solution 52, except for those following the steps for preparing sample E, for example selective lysis of erythrocytes and/or staining of leukocytes. Preferably, no additional dilution is performed for a WIC measured leukocyte concentration in sample E comprised between 300 leukocytes per microlitre and 7000 leukocytes per microlitre.

A second section 72 of the curve corresponds to a second operating procedure, in which test solution ST is obtained by a single direct dilution, from sample E or from an intermediate solution. Preferably, a single direct dilution is performed for a WIC measured leukocyte concentration in sample E comprised between 7000 leukocytes per microlitre and 50,000 leukocytes per microlitre.

A third section 73 of the curve corresponds to a third operating procedure, in which test solution ST is obtained by sampling intermediate solution S2 prepared from sample E. Preferably, this third operating procedure is performed for a measured WIC leukocyte concentration of sample E exceeding 50,000 leukocytes per microlitre.

Thus, dilution step 330 performs an automatic adjustment of the leukocyte concentration, during the preparation of test solution ST intended for imaging. By application of a dilution ratio D calculated as a function of the WIC measurement, for example according to the calculation presented above, it is possible to obtain an optimal leukocyte concentration of test solution ST for visual measurements.

An optimal leukocyte concentration of test solution ST corresponds to a surface density of elements of interest on optical plane PO of optical chamber 4 suitable for clearly distinguishing the leukocytes and performing relevant visual measurements, at the end of centrifugation step 400 (described below).

Preferably, dilution step 330 according to dilution ratio D (optionally comprising an adjustment dilution) ultimately permits obtaining a target surface density of leukocytes on optical plane PO comprised between 20 and 1000 leukocytes per square millimetre, once the leukocytes have been moved on optical plane PO.

Still more preferentially, the target surface density of leukocytes obtained on optical plane PO is comprised between 24 and 800 leukocytes per square millimetre.

Figure 7:
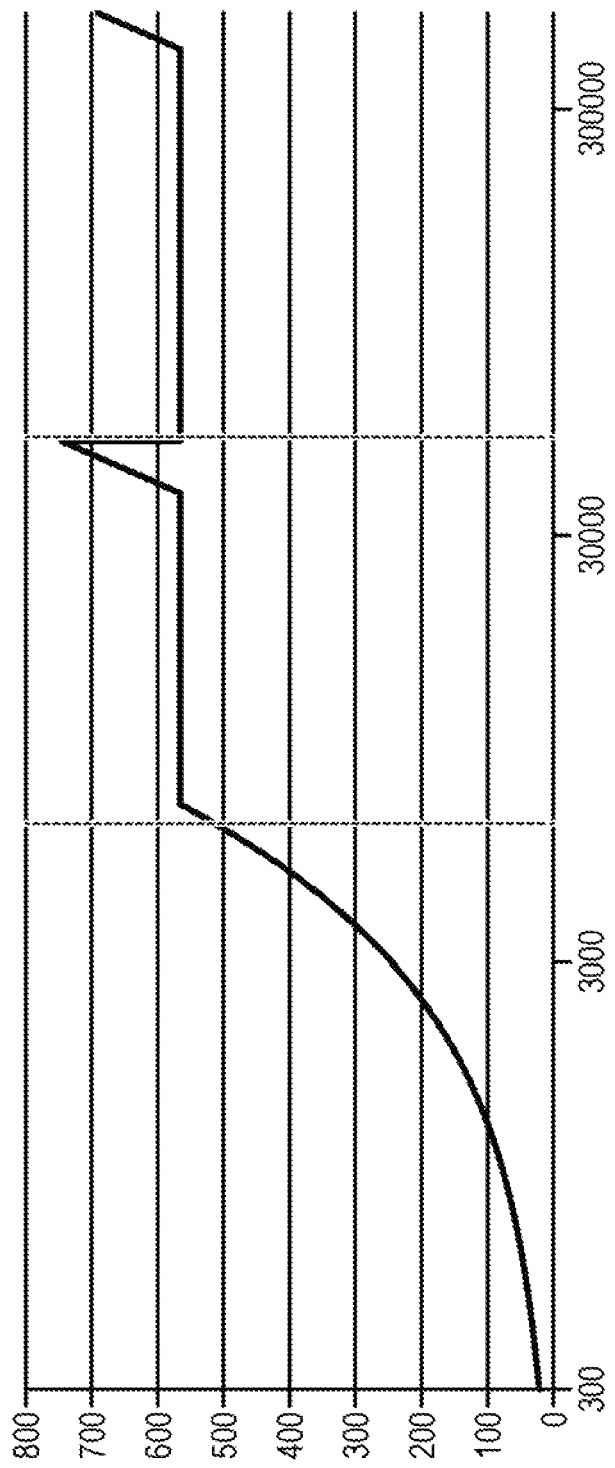
FIG. 7 is a graph that shows on the y-axis the surface density in leukocytes per square millimetre obtained on the optical plane of the optical chamber at the end of centrifugation of the test solution, and on the x-axis the measured leukocyte concentration in the initial sample, according to the same example of embodiment.

FIG. 7 comprises a curve 81 representative of the surface density of leukocytes obtained on optical plane PO of optical chamber 4 (for example at the end of the centrifugation of step 400 of the method illustrated in FIG. 4), expressed in leukocytes per square millimetre, as a function of the WIC measured leukocyte concentration in sample E.

In this example, the surface density of leukocytes on optical plane PO remains less than 800 leukocytes per square millimetre.

Three specific points of the curve of FIG. 6 are referenced:
Point A1 corresponds to a WIC measured concentration of leukocytes equal to 10,000 leukocytes per microlitre. The dilution ratio is equal to 18. The surface density of leukocytes obtained on optical plane PO is equal to 570 leukocytes per square millimetre.

Point A2 corresponds to a WIC measured concentration of leukocytes equal to 50,000 leukocytes per microlitre. The dilution ratio is equal to 90. The surface density of leukocytes obtained on optical plane PO is equal to 750 leukocytes per square millimetre.

Point A3 corresponds to a WIC measured concentration of leukocytes equal to 200,000 leukocytes per microlitre. The dilution ratio is equal to 360. The surface density of leukocytes obtained on optical plane PO is equal to 570 leukocytes per square millimetre.

A target surface density of 570 leukocytes per square millimetre is considered to be very satisfactory to have sufficient leukocytes available in the image, while limiting their superimposition.

Dilution ratio D is determined preferably as an affine function of the leukocyte concentration in initial sample E (WIC measured concentration), at least for a part of the possible value ranges of leukocyte concentration of the initial sample, as illustrated in FIG. 6 described above. Thus, it is possible to obtain a surface density very close to 570 leukocytes per square millimetre on images $I_n$, independently of the leukocyte concentration of sample E.

The surface coverage rate of the elements of interest (leukocytes here) in images $I_n$ obtained at the end of imaging step 500 is preferably comprised between 0.1% and 15%, for leukocytes for which a mean characteristic size is comprised between 5 and 15 micrometres. "Surface coverage rate" here means the number of pixels of the image corresponding to leukocytes, divided by the total number of pixels of the image.

For example, the mean coverage rate of leukocytes in images $I_n$ is close to 4%, for human leukocytes of characteristic size equal to 9.2 micrometres. Such a coverage rate of 4% is considered to be very satisfactory to have sufficient leukocytes available in the image while limiting their superimposition.

Via the adjustment dilution in step 330, the leukocyte surface density is satisfactory, in view of measurements on the images obtained from imaging. On the one hand, the case represented on the left of FIG. 2, in which the leukocyte coverage rate is insufficient to perform statistically relevant measurements—for example measurements of leukocyte morphology and differentiation—is avoided, and, on the other hand, the case represented on the right of FIG. 2, in which the number of leukocytes per image is too high and does not allow clearly distinguishing the morphological characteristics of the leukocytes is also avoided. The number of leukocytes obtained per image (here within images $I_n$) at the end of imaging step 500, is a function of the surface leukocyte density per square millimetre on optical plane PO, and is also a function of the surface of optical plane PO visible in an image $I_n$.

The surface of optical plane PO visible in an image $I_n$ is itself a function of the magnification of an optical sensor of the imaging device used. Here, the system of FIG. 1 comprises a photographic device 5 endowed with an objective 51 whose magnification is comprised between 10× an 50×. Thus, the number of leukocytes per image $I_n$ is preferably comprised between 5 and 200, and still more preferably between 50 and 200. A number of leukocytes per image comprised between 50 and 200 permits achieving a good compromise between, on the one hand, avoiding a superimposition of leukocytes in images $I_n$ (which interferes with leukocyte differentiation) and, on the other hand, improving the statistical accuracy of the subsequent visual measurements.

A number of leukocytes per image comprised between 140 and 160, for example equal to 150, is considered optimal for the compromise between a low amount of superimposition of leukocytes and a good statistical precision of the visual measurements.

A surface coverage rate of image $I_n$ by leukocytes is preferably comprised between 0.15% and 5%. The leukocytes have a mean characteristic size equal to 9.2 micrometres.

An additional advantage of the secondary dilution proposed here (step 330) is an automated determination of the dilution ratio D, once certain parameters have been defined upstream: here, the volume of solution which corresponds to the field of view of an image acquired by photographic device 5, as well as the optimal leukocyte concentration which corresponds to the desired leukocyte surface density on optical plane PO of the optical chamber 4.

As a result of the steps above, a volume of test solution ST is available. In order to perform the imaging, this volume is poured into channel 42 of optical chamber 4.

Preferentially, as indicated above, a centrifugation 400 of optical chamber 4 is then performed, so as to bring the leukocytes (previously visually labelled by staining) onto the same optical plane PO of the optical chamber. Centrifugation step 400 is preferably performed automatically by a centrifugation unit (not shown) integrated in the imaging system of FIG. 1. Centrifugation is, for example, performed by rotating optical chamber 4 around the direction parallel to optical plane PO.

Advantageously, the centrifugation time is comprised between 5 seconds and 5 minutes. Still more advantageously, the centrifugation time is comprised between 10 seconds and 1 minute.

Once centrifugation is completed, a partial cleaning is performed in the chamber in order to remove the stains in the background and allow the elements of interest to appear fixed onto the glass support so that processing unit 6 commands photographic device 5 to take an image of solution ST contained in channel 42.

The image obtained I is recorded in the memory of the processing unit.

Preferably step 500 comprises a plurality of acquisitions of images $I_n$. The moving means are activated so that photographic device 5 adopts several successive positions, by moving parallel to reading axis A. Thus, the field of view of device 5 sweeps along the length of reading channel 42.

In one possible example, around 80 images of test solution ST are acquired in all, over a duration of around 30 seconds. Thus, the centrifugation time of step 400 added to the imaging time of step 500 advantageously does not exceed 2 minutes.

Notably, it is not necessary to wait for the elements of interest to sediment on optical plane PO before imaging, thanks to centrifugation 400. Thus, the total acquisition time for images $I_n$ is greatly reduced, which allows visual measurements that are both statistically relevant and fast.

At optional step 600, a visual measurement is performed from image I or images $I_n$. The visual measurement comprises, in the present example, a leukocyte differential count, to obtain a statistical distribution of leukocytes in sample E (and especially the leukocytes of an individual) among the five subgroups: lymphocytes, monocytes, basophils, eosinophils and neutrophils.

Optimally, the visual measurement performed from image I or images $I_n$ also comprises a qualitative characterization of the elements of interest and/or other pathological or non-pathological elements visible in the images.

As examples of qualitative characterization, a distinction can be made in the images between pathological cells (such as blasts or lymphomas) and non-pathological cells. The detection of pathological cells can concern the elements of interest (leukocytes here) and/or other elements visible in the image.

The qualitative characterization can especially include an identification of pathological elements in the images, such as tumour cells, parasites (malaria, etc.) or bacteria characteristic of an infectious syndrome such as sepsis.

The visual measurements following the adjustment dilution of the invention permit such a qualitative characterization—unlike, for example, flow cytometry measurements—while ensuring a satisfactory analysis speed and good statistical precision of the measurements.

The use of such visual measurements, combined with the adjustment dilution described previously, therefore improves the relevance of the clinical data provided to the clinician at the output of the method, while ensuring an optimal analysis speed.

Figure 8:
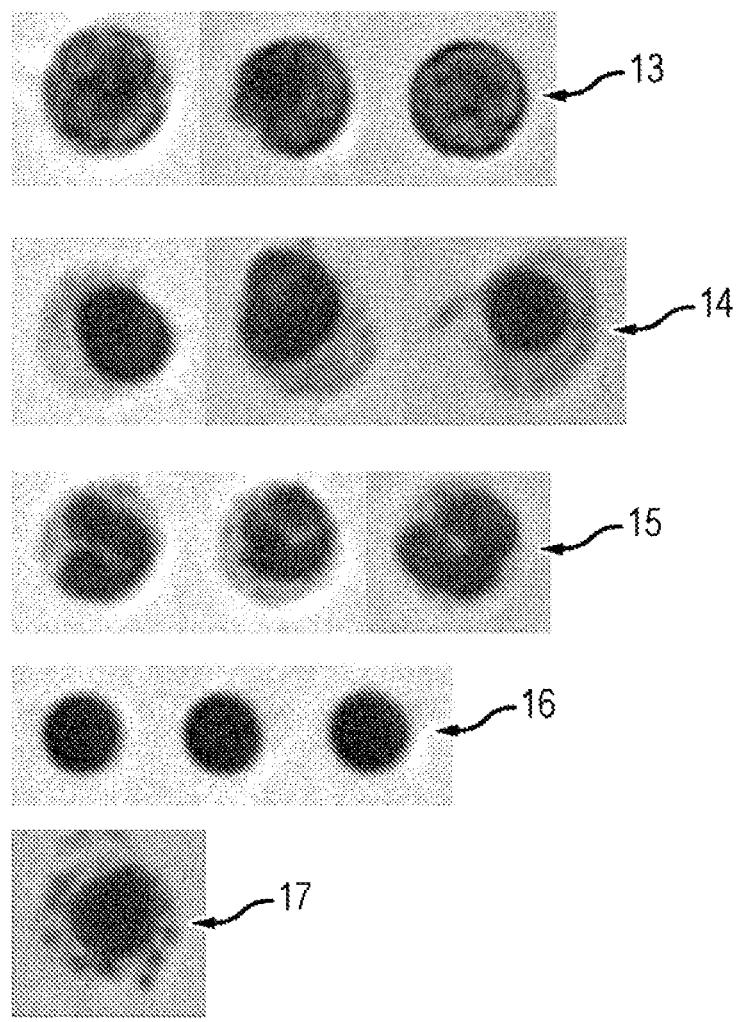
FIG. 8 is an image of the various subgroups of leukocytes subjected to staining in a blood sample.

FIG. 8 compares the views of leukocytes belonging to five distinct subgroups 13, 14, 15, 16 and 17, in an image obtained at the end of step 500 after leukocyte staining. These subgroups respectively correspond to eosinophils, monocytes, neutrophils, lymphocytes and basophils. The leukocyte differential count takes into account different interesting morphological characteristics (dimensions) of the cells: for example, eosinophils have a nucleus with several lobes and a cytoplasm with granulations, lymphocytes have a single nucleus occupying the majority of the cell volume, and neutrophils have a nucleus with three lobes.

For example, the results of the differential count are shown graphically, in an graphic interface connected to processing unit 6, in the form of a cloud of points on which clusters of points are labelled. Histograms can also be exported concerning the size and volume of the elements of interest, the size of the nucleus of the elements of interest, etc.

The visual element thus comprises an automatic analysis of the images resulting from the imaging. Very advantageously, the analysis performed by the computer can be verified by a human observer. Such a verification is particularly relevant if there is an anomaly in the results of the visual measurement.

Indeed, unlike optical measurements such as diffraction measurements, image analysis is verifiable by an observer. Anomalies or artifacts can thus be detected and "black box" operation of the visual measurement is avoided.

According to a variant, the images acquired using images 500 are recorded and transmitted to a remote server that performs the visual measurements.

Another advantage of visual measurement on a sample with adjustment dilution is to ensure the statistical precision and reliability of the measurements: via the adjustment of dilution ratio, the number of elements of interest in each image is close to an optimal number.

Figures 9, 10:
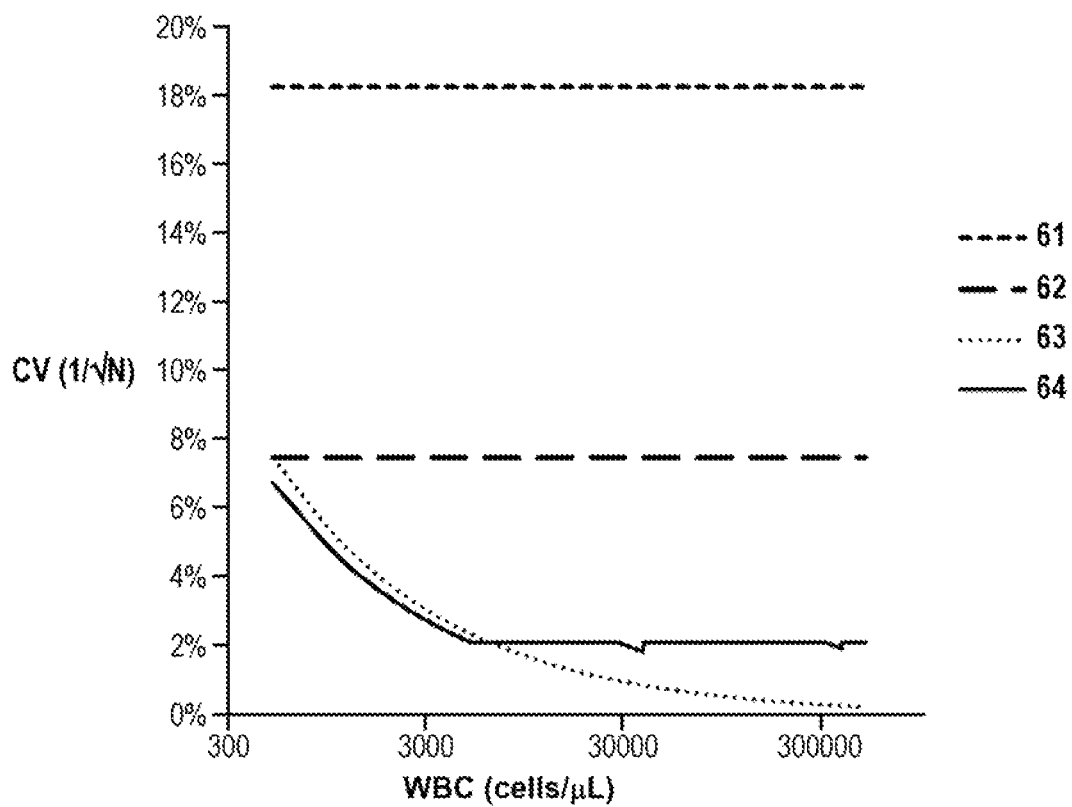
FIG. 9 is a table comprising performance data for the leukocyte differentiation measurement, according to subgroups of leukocytes and according to the type of measurement used for the differentiation.
FIG. 10 is a graph representing the statistical performance of the leukocyte differentiation (on the y-axis) only for subgroups of lymphocytes, according to the lymphocyte concentration of the initial sample (x-axis) and according to the type of measurement used for the differentiation.

The table of FIG. 9 gives the statistical coefficient of variation of the leukocyte differentiation measurement obtained at the end of step 600 for each of five subgroups of leukocytes, depending on the type of differentiation measurement implemented.

The values are given for a WIC leukocyte concentration of the blood sample of 8000 cells per microlitre, and for 80 images with a target number of 150 cells per image. At this concentration, the performances of the method with visual measurements are similar to those of flow cytometry, with the additional advantage of a better verifiability of results ("black box" operation is avoided).

FIG. 10 shows the evolution of the statistical coefficient of variation of the differentiation results, for the case of lymphocytes, depending on the leukocyte concentration in the blood sample. Curve 61 corresponds to a "manual" slide review by an operator working with the naked eye. Curve 62 corresponds to an automated slide review similar to the method of document WO 2010/126903 discussed previously. Curve 63 corresponds to a measurement by flow cytometry and diffractive optics. Finally, curve 64 corresponds to the visual measurements of the method described above in relation to FIG. 4.

As shown in FIG. 10, adjusting the dilution ratio (to bring the leukocyte concentration of test solution ST after dilution to an optimal concentration) increases the statistical precision compared to manual or automated slide review techniques, and reduces the proportion of samples that must be subjected to human visual analysis. The optimal leukocyte concentration of test solution ST preferably corresponds to a target surface density, denoted WPD, of between 20 and 1000 leukocytes per square millimetre on optical plane PO of optical chamber 4 at the end of centrifugation, as indicated above.

Moreover, the search time for elements of interest in the image is reduced compared to the automated slide review technique, especially in the case where cells other than the cells of interest have been lysed. It is not necessary to look for a reading zone in a sample, nor to extract a plurality of images at high magnification to perform morphological measurements. The method of the invention therefore also allows increasing sample processing speed.

Figure 11:
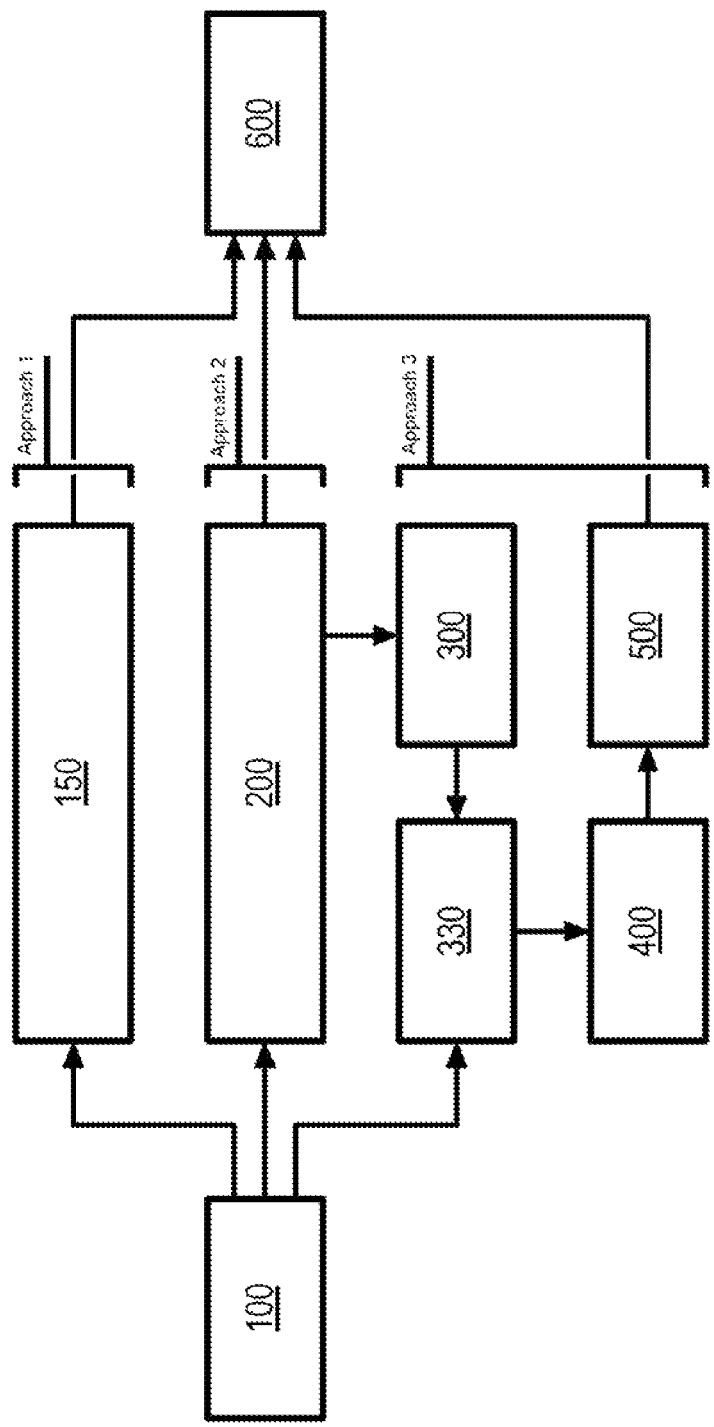
FIG. 11 shows the steps corresponding to three measurement approaches for the analysis of a blood sample.

FIG. 11 is an overview of the steps for processing a blood sample according to a preferred embodiment, comprising the steps of the method of FIG. 4.

Three different measurement approaches are used:
An approach 1 consisting of impedance count 150 of erythrocytes using a cell with an orifice of 78 μm, from which a measurement is determined of the erythrocyte and thrombocyte concentration of sample E obtained at the end of sampling 100;
An approach 2 consisting of impedance count 200 of leukocytes using a cell with an orifice of 100 μm, from which a WIC measurement is determined of the leukocyte concentration of sample E obtained at the end of sampling 100;
An approach 3 comprising, in accordance with the method described above in relation to FIG. 4, a determination 300 of the need for an adjustment dilution, a possible adjustment dilution 330 to obtain a test solution, a centrifugation 400 of the test solution and an imaging 500.

At step 600, the calculation unit collects the measurements originating from three methods 1, 2 and 3 and performs a series of analyses comprising the visual measurements described above.

An additional advantage of visual measurement is to allow selective analysis of any type of elements of interest distinguishable in an image. Visual measurement is thus versatile, although it is preferably applied here to leukocytes in combination with an adjustment dilution of the test solution. Visual measurement can be, for example, transposed to erythrocytes or thrombocytes, and more generally to any type of element of interest comprised in a body fluid.

Thus, if the results of the impedance count of erythrocytes in method 1 are determined to be abnormal, there is advantageously provided a "reflex approach" of measurement consisting of performing an erythrocyte count using visual measurements. For example, optical chamber 4 and photographic device 5 are used to perform imaging in which the erythrocytes are labelled.

The invention claimed is:

1. An imaging method for imaging a body fluid sample for visual measurement relating to leukocytes of the sample, said method comprising the following steps:

an acquisition of the leukocyte concentration of a solution derived from the sample, resulting in obtaining a measured concentration of the leukocytes in the sample;

a dilution of a test solution derived from the sample according to a dilution ratio D determined as a function of the measured concentration of leukocytes in the sample, so as to bring the leukocyte concentration of the test solution to an optimal leukocyte concentration;

a transfer of the test solution into the optical chamber, and a rotation of optical chamber by a centrifugation unit so as to align the leukocytes of the test solution on an optical plane comprised in the optical chamber, the optical plane being perpendicular to a direction of thickness of the optical chamber, wherein the optimal concentration of leukocytes for the test solution corresponds to a target surface density on the optical plane comprised between 20 leukocytes per square millimetre and 1000 leukocytes per square millimetre after aligning the leukocytes with the optical plane, and wherein the dilution ratio D is comprised between 10 and 1000 or is calculated using the following formula: D=WIC*h/WPD, wherein WIC is the measured concentration of the leukocytes in the sample, h is a height of the optical chamber and WPD is the target surface density on the optical plane, an imaging, by an imaging device, of the test solution on the optical plane.

2. Imaging method according to claim 1, wherein the optical chamber is rotated for a duration comprised between 5 seconds and 5 minutes.

3. Imaging method according to claim 1, wherein the acquisition comprises a non-visual measurement on an intermediate solution derived from the sample.

4. Imaging method according to claim 1, wherein the acquisition step comprises a measurement of the absorbance at a predetermined wavelength on an intermediate solution derived from the sample.

5. Imaging method according to claim 1, wherein the imaging step comprises a plurality of image acquisitions at distinct positions of the imaging device relative to the optical chamber, the imaging device moving along the same direction between two consecutive positions.

6. Imaging method according to claim 1, the method comprising an additional step of preparing the test solution comprising cell separation and/or selective chemical and/or physical lysis to sort the cells and retain the leukocytes.

7. Imaging method according to claim 1, comprising an additional step of preparing the test solution comprising a permeabilization of the leukocyte membranes and/or a distinctive staining of the leukocytes.

8. Imaging method according to claim 1, comprising a visual measurement performed on the test solution image, the visual measurement comprising a leukocyte differential count, a result of said count comprising a distribution of the leukocytes in the sample among a plurality of subgroups.

9. Imaging method according to claim 1, wherein the image obtained at the end of imaging has a total number of leukocytes comprised between 5 and 200.

10. An imaging system for imaging a body fluid sample, the system being configured to implement an imaging method according to claim 1, said system comprising:

a measurement device for the leukocyte concentration of a solution obtained from a body fluid sample, an imaging device, a processor configured to control the imaging device and to receive, from measurement device, a measured concentration of leukocytes of the sample, the processor being further configured to calculate a dilution ratio depending on said measured concentration, a dilution device designed to perform a dilution of a solution derived from a body fluid sample according to a determined dilution ratio, an optical chamber designed to receive a test solution derived from a body fluid sample, a centrifugation unit configured to rotate the optical chamber containing the test solution.

11. Imaging system according to claim 10, wherein the leukocyte concentration measurement device comprises a micro-orifice cell, designed to determine a leukocyte count by impedance.

12. Imaging system according to claim 10, wherein the imaging device comprises movement means designed to move an objective of the imaging device along a reading axis of the optical chamber.

13. Imaging system according to claim 10, wherein the optical chamber comprises a leukocyte support wall delimiting an optical plane, the leukocyte support wall having a thickness comprised between 0.05 millimetres and 0.5 millimetres, the centrifugation unit being configured so as to bring the leukocytes of the test solution onto said optical plane.

14. A non-transitory computer-readable storage medium storing code instructions which, when the code instructions are executed by a processing unit, lead the processing unit to implement an imaging method in accordance with claim 1.

* * * * *